United States Patent [19]
Waterman

[11] Patent Number: 5,410,769
[45] Date of Patent: May 2, 1995

[54] BILATERAL HEAD AND ARMS IMMOBILIZATION SUPPORT FOR MEDICAL PURPOSES AND METHODS

[75] Inventor: Glenn N. Waterman, Salt Lake City, Utah

[73] Assignee: Diacor, Inc., Salt Lake City, Utah

[21] Appl. No.: 134,143

[22] Filed: Oct. 8, 1993

[51] Int. Cl.⁶ .................. A47C 20/02; A47G 9/00
[52] U.S. Cl. ............................. 5/632; 5/643; 5/646
[58] Field of Search ............ 5/632, 646, 647, 636, 5/637, 640, 643, 1, 623; 128/878, 879

[56] References Cited

U.S. PATENT DOCUMENTS

| | | | |
|---|---|---|---|
| 1,869,278 | 7/1932 | Ramelli | 5/634 |
| 1,919,908 | 7/1933 | Schmidt | 5/613 |
| 3,220,019 | 11/1965 | Nelson | 5/610 |
| 3,476,256 | 11/1969 | Anderson | 5/646 |
| 3,724,004 | 4/1973 | Behrens | 5/601 |
| 3,795,018 | 3/1974 | Broaded | 5/623 |
| 4,373,222 | 2/1983 | Wolfe et al. | 5/623 |
| 5,214,814 | 6/1993 | Eremita et al. | 5/646 |
| 5,375,276 | 12/1994 | Nelson et al. | 5/623 |

Primary Examiner—Alexander Grosz
Attorney, Agent, or Firm—Foster & Foster; Lynn G. Foster

[57] ABSTRACT

A bilateral immobilization support is disclosed for placing and retaining the arms of a patient in an overhead position during patient examination, diagnostic procedures and/or radiation therapy. The adjustability of the wrist and upper arm supports carried upon a base provides for immediate accurate sizing adjustment in location consistent with the needs of the patient and continuing comfort for the duration of use. The initial settings of the support are visually observable and readily reproducible at subsequent times for the same or similar purposes during which the arms of the patient are immobilized and comfortably supported out of alignment with the area of the body being subjected to a medical procedure. The patient is not restrained, but with both arms above the head the patient inherently tends to relax and remain in a single position.

27 Claims, 4 Drawing Sheets

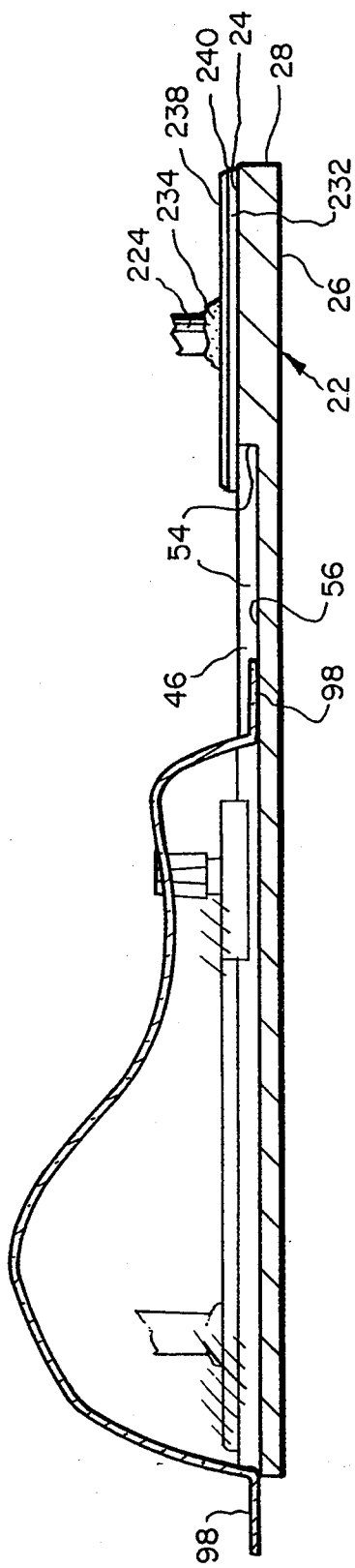
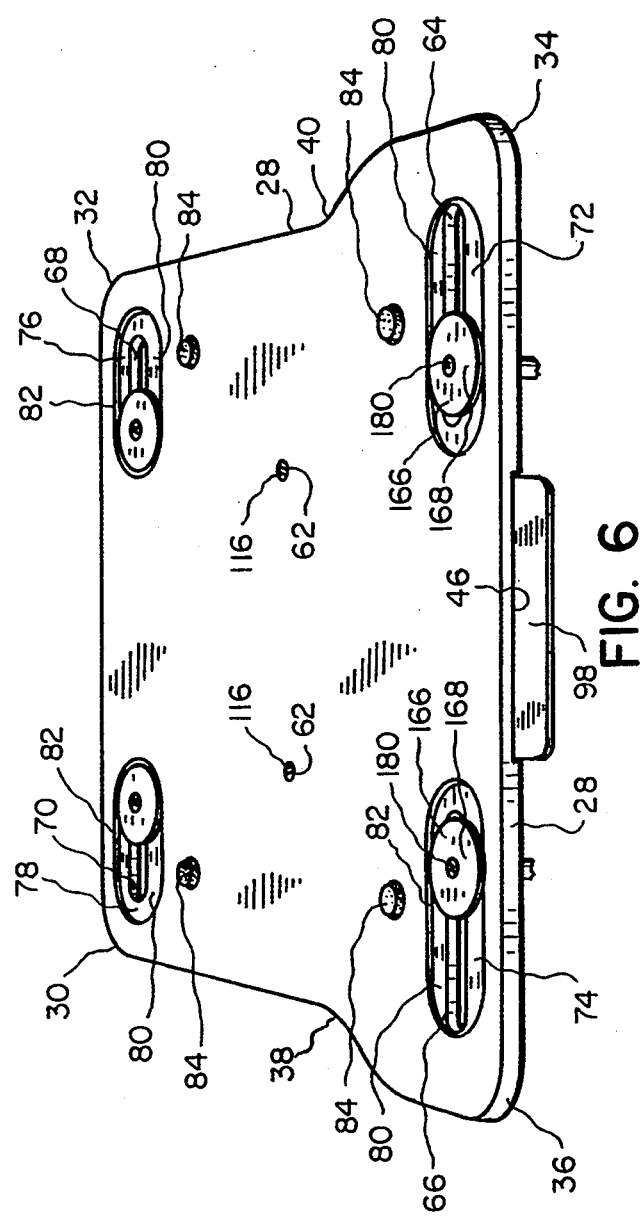

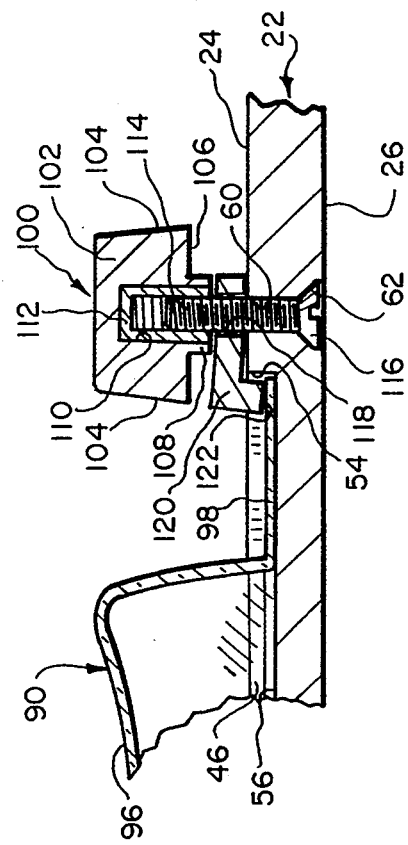
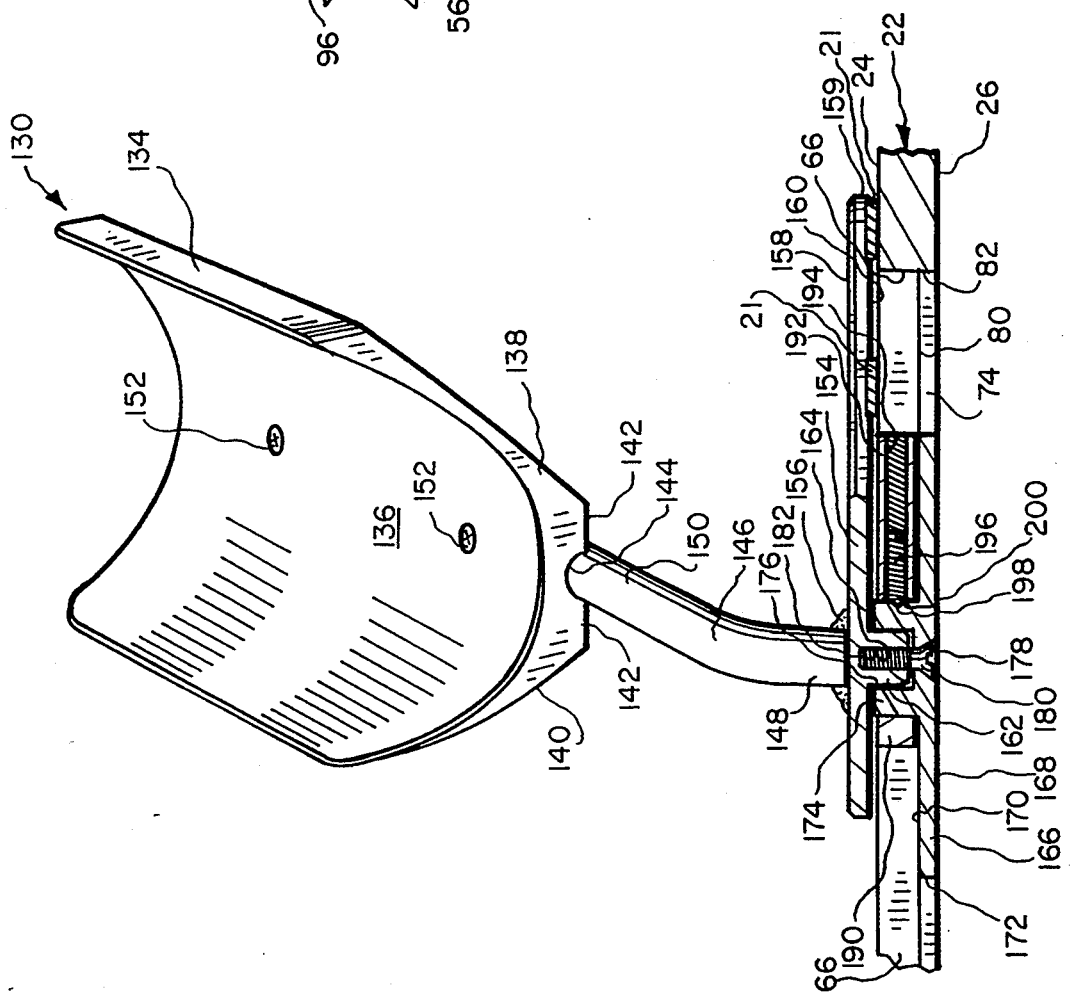
FIG. 5
FIG. 4

BILATERAL HEAD AND ARMS IMMOBILIZATION SUPPORT FOR MEDICAL PURPOSES AND METHODS

FIELD OF INVENTION

The present invention relates generally to immobilization of a medical patient and more specifically to a bilateral immobilization support, and related methods, by which the arms of a patient are immobilized in an overhead position without constraining the patient to assist in various medical procedures including but not limited to patient examination and radiation therapy.

BACKGROUND

In the past, without an ancillary arm support device placement and retention of the arms away from a body location being subjected to examination, diagnostic procedures or radiation has presented difficulties. Thus, use of an arm support has become the treatment of choice.

Nevertheless, prior to the present invention such arm supports fail to provide full arm immobilization, lack versatility and accuracy, result in substantial discomfort to the patient and do not facilitate reproducible repetitive use with the same patient at different points in time.

BRIEF SUMMARY AND OBJECTS OF THE PRESENT INVENTION

In brief summary, the present invention overcomes or substantially alleviates the aforementioned problems of the prior art and comprises a bilateral immobilization support for placing and retaining the arms of a patient in an overhead position during patient examination, diagnostic procedures, and/or radiation therapy. The adjustability of the support provides for immediate accurate sizing consistent with the needs of the patient and continuing comfort for the duration of use. The initial settings of the variables of the support are readily reproducible at subsequent times for the same or similar purposes during which the arms of the patient are immobilized and comfortably supported out of alignment with the area of the body being subjected to a medical procedure. The patient is not restrained, but with both arms above the head the patient inherently tends to relax and remain in a single position. In its presently preferred form, the present inventive support includes the following features and characteristics:

1. Wrist and upper arm positioning carriages are carried by the support and are easily relocated and adjusted to fit the needs and comfort of the patient;
2. The arm carriages accommodate adjustment by both translation and rotation and a plurality of detent positions are provided;
3. The wrist carriages also accommodate adjustment by both translation and rotation to provide comfortable support;
4. All carriage settings for a given patient are indexed to allow a patient's position to be later reproduced;
5. An indexed adjustable head carriage insures a reproducible and comfortable head and neck positions during therapy;
6. The support is preferably made from lightweight material, which accommodates easy cleaning and maintenance;
7. The support fits or is congruent with simulators, accelerators and CT scanners; and
8. Non-skid feet prevent the support from sliding.

It is a primary object of the present invention to provide a patient support mechanism which overcomes or substantially alleviates problems of the prior art.

Another significant object of the present invention is to provide a bilateral immobilization support, and related methods, for placing and retaining the arms of a patient in a comfortable overhead position during radiation or at similar diagnosis or treatment.

A further important object of the present invention is to provide a patient support mechanism which is adjustable for immediate, accurate sizing consistent with the needs of a given patient.

An additional dominant object of the present invention is the provision of a patient support accommodating radiation or similar diagnosis or treatment where continuing comfort is provided to the patient during the entire duration of the therapy.

An additional paramount object of the present invention is the provision of a novel patient support mechanism which is adjustable to the size and needs of the patient providing initial settings of variable features of the support which can readily be reproduced later to accommodate subsequent radiation treatments.

An additional primary object of the present invention is to provide a patient support system for radiation therapy by which the arms of the patient are immobilized and comfortable supported out of alignment with the radiation being imposed upon the patient.

It is an object of significance to provide a patient arm support mechanism for overhead placement of both arms so that the patient tends to remain in one position during use of the mechanism.

A further important object is the provision of a novel patient support system having one or more of the following features and characteristics:

provision of wrist and upper arm positioning carriages which are easily relocated and adjusted to fit the needs of the patient;

provision of arm carriages and wrist carriages which accommodate adjustment to the needs of the patient by both translation and rotation and which also provide for prolonged patient comfort;

a further paramount object is the provision of a patient support of the type in question wherein all carriage settings for a given patient are indexed to allow subsequent reproduction;

provision of an indexed adjustable head carriage which insures reproducibility and comfort to the patient during therapy;

provision of a support mechanism which is lightweight and easily cleaned and maintained;

provision of a support which fits and is congruent with equipment for radiation therapy;

provision of a support which is stable during use;

provision of a support mechanism having arm-receiving carriages which are locatable and contoured to comfortably receive the arms of the patient in overhead positions.

These and other objects and features of the present invention will be apparent from the detailed description taken with reference to the accompanying drawings.

BRIEF DESCRIPTION OF THE DRAWINGS

FIG. 2 is a cross-section taken along line 2—2 of FIG. 1;

FIG. 4 is a cross-sectional view taken along lines 4—4 of FIG. 1;

FIG. 5 is a cross-section taken along lines 5—5 of FIG. 1; and

FIG. 6 is a bottom perspective of the mechanism of FIG. 1.

DETAILED DESCRIPTION OF THE ILLUSTRATED EMBODIMENT

Figure 1:
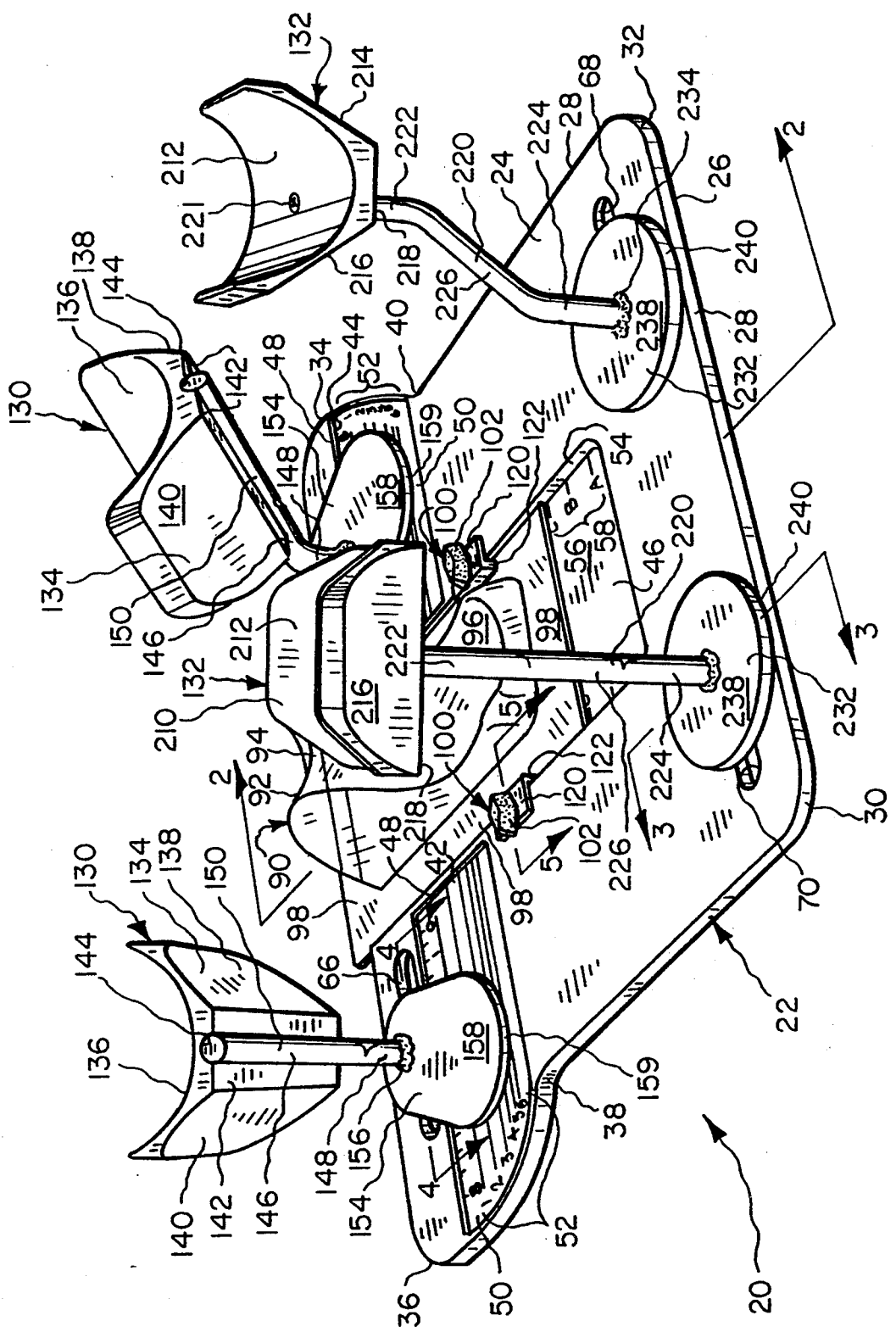
FIG. 1 is a perspective representation of one embodiment of a mechanism for securing the human body in a fixed position during radiation treatment with the shoulders, arms and hands comfortably positioned remote from the treatment site.

Reference is now made to the drawings wherein like numerals are used throughout to designate like parts. Specifically, with reference to FIG. 1, a portable patient bilateral immobilization support mechanism, generally designated 20, embodying the principles of the present invention is depicted. The bilateral immobilization support mechanism 20 is adapted for manual movement or transportation from place to place and for convenient storage on a shelf, in a closet, or elsewhere during periods of non-use. It can readily be used with most medical patients ranging from the young to the elderly, independent of the physical make-up and characteristics of a given patient.

Support mechanism 20 comprises a relatively thin, planar static or stationary base or board 22. Base 22 comprises a wall having a substantially uniform thickness throughout, except as otherwise indicated herein. Preferably, base 22 comprises a lightweight synthetic resinous material such as acrylic, which is easily cleaned and maintained. The base 22 comprises a top, flat surface 24, a bottom, generally flat planar surface 26, which is parallel to top surface 24 and a blunt edge 28. Blunt edge 28 is illustrated as being perpendicular to top and bottom surfaces 24 and 26. Edge 28 is rounded at outside corners 30, 32, 34, and 36. Peripheral edge 28 also comprises inside rounded corners 38 and 40.

Top surface 24 of the base 22 is interrupted by three recesses or indentations, i.e., recesses 42 and 44 shown in the upper left hand and upper right hand portions of the base 22 as seen in FIG. 1 and an upper central sunken or recessed region 46. Recesses 42 and 44 are illustrated as being identical, one to the other, but of opposite hand. Recess 46 is illustrated as having a depth greater than the depth of recesses 42 and 44. Recess 42 comprises a shoulder 48 and a flat exposed surface 50 upon which an exposed set of measuring or indexing graduations or a scale 52 is visually presented for purposes yet to be explained. Similarly, recess 44 comprises a shoulder 48 and a flat exposed surface 50 upon which a set of exposed measuring or indexing graduations or a scale 52 is depicted, for example, by engraving or by using coated silkscreened plastic with adhesive backing.

Recess 46 comprises a deeper shoulder 54 and a flat exposed surface 56 parallel to the top surface 24 upon which graduations 58 are depicted, for example, by engraving or by using coated silkscreened plastic with adhesive backing, for purposes yet to be explained.

Shoulders 48 of recesses 42 and 44 and shoulder 54 comprise three sides of the recess with which each is associated, each recess opening at the peripheral edge 28. Thus, each recess 42, 44, and 46 are generally rectangular in their configuration.

As best illustrated in FIG. 5, two bores 60 extend through the base 22 between the bottom and top surfaces 26 and 24, essentially parallel to the edge 28. Each bore 60 is counter-bored at 62. The purpose of the bores 60 will be explained later.

The bottom surface 26 of the base 22 is interrupted by four elongated recesses 72, 74, 76, and 78. As can be seen from FIG. 6, each recess 72, 74, 76, and 78 symmetrically surrounds the elongated slots 64, 66, 68, and 70, respectively, each recess 72, 74, 76, and 78 comprising a flat indented exposed surface 80 and a surrounding shoulder 82. The purposes of recesses 72, 74, 76, and 78 will be explained hereinafter.

Four spaced elastomeric, anti-displacement pedestals 84 are illustrated in FIG. 6 as being adhesively secured to the bottom surface 26 of the base 22 to accommodate stable placement upon any suitable flat surface, such as a patient examination table.

As best illustrated in FIG. 1, recess 46 is adapted to receive a relocatable, adjustable head and neck rest, holder, tray, or support, generally designated 90. Head and neck rest 90 comprises an elevated projection 92 which comprises a concavely configured central region 94 configured to fit and contiguously receive the neck of a patient. The upwardly projecting portion of the head and neck rest 90 is interiorly hollow, as best illustrated in FIG. 2. The head and neck rest 90 further comprises a slightly elevated centrally concavely configurated segment 96, configurated to fit and contiguously receive the back of the head of the patient.

As best illustrated in FIG. 2, the head and neck rest 90, as illustrated, is formed of a thin wall contoured single piece formed by conventional injection or vacuum molding techniques, which may be transparent for improved observation. The molded synthetic resinous material, while projecting upwardly in the central region thereof, as explained above, comprises a flat four-sided peripheral flange 98, the thickness of which is illustrated as being substantially less than the depth of shoulder 54. The underside of the flange 98 rests contiguously against the surface 56 of the recess 54 and has a width and length consistent with the width and length of the recess 46. Thus, flange 98 supports the rigid neck support segment 92 and head support segment 96 in the position generally illustrated in FIG. 1.

Without constraint, the neck and head rest 90 would, when horizontally flat as illustrated in FIG. 1 be capable of sliding to and fro within recess 46 unconstrained. To accommodate selective relocation of the neck and head rest 90, two thumb screw clamps, each generally designated 100, are provided. Since each of the two thumb screw clamps 100 are identical, though of opposite hand, only one will be described. In this regard, reference is now made to FIG. 5, which illustrates the thumb screw clamp 100 shown on the left in FIG. 1. Thumb screw clamp 100 comprises a manually rotatable knob 102, illustrated as being formed of solid synthetic resinous material which is rigid and shape-retaining. The sides 104 are elongated and converging in both directions. The bottom surfaced 106, which is centrally interrupted by downwardly extending boss 108 through which an upwardly directed lined bore 110 extends. An internally threaded blind bore insert 112 is press-fit into blind bore 110 and receives the threaded end 114 of a countersunk screw 116. Screw 116 extends through vertical bore 60 in the base 22. The threaded shaft 114 of the screw 116 also extends through an aperture 118 in an L-shaped clamp member 120. The bore or aperture 118 is disposed in the long leg of the L while the short leg, at edge 122 contiguously and forcibly engages the flange 98, when the knob 102 is fully tightened.

When both thumb screw clamps 100 are fully tightened, the head and neck rest 90 is held in a selected position within the recess 46. To relocate and adjust the position of the head and neck rest 90 to any given patient, the knobs 102 of the two thumb screw clamps 100 are loosened, the head and neck rest 90 appropriately positioned in respect to the recess 46 and the loosened thumb screw clamps 100, following which the two knobs 102 are tightened, causing the two edges 122 to firmly downwardly clamp against the flange 98 of the head and neck rest 90. In this way, the head and neck rest 90 can be rectilinearly translated to and fro within the recess 46 to selectively reposition and to secure the head and neck rest 90 in the desired position by tightening the thumb screw clamps 100.

It is to be appreciated that given the nature and make-up of head and neck rest 90 that it is within the principles and purposes of the present invention to provide several similar head and neck rests of different sizes congruent with the ranges in the size and shape of the necks and heads of various patients to be accommodated by the patient bilateral immobilization support mechanism 20.

For a given patient, once the head and neck rest 90 is clamped by thumb screw clamps 100 into a desired position, the indexing scale 58 can be appropriately read and recorded on the patient's chart for use in positioning the head and neck rest during subsequent medical procedures.

As best shown in FIG. 1, the portable patient bilateral immobilization support mechanism 20 comprises right and left elevated relocatable adjustable upper arm carriages, each generally designated 130 and right and left elevated relocatable repositionable wrist support carriages, each generally designated 132.

Since right and left carriages 130 are identical, though of opposite hand, only one will be described. Similarly, since right and left wrist carriages 132 are identical though of opposite hand, only one will likewise be described.

Upper arm carriage 130 comprises a contoured cradle 134, which has a contoured concavity 136 disposed diagonally, i.e., at an angle to both the horizontal and the vertical to accommodate facile, comfortable reception of the upper arm when placed overhead in an entirely comfortable fashion. The cradle 134 comprises exterior convergingly tapered flat wall surfaces 138 and 140, which are interconnected by a lower surface 142, which is centrally interrupted by a circular groove 144, which is co-axial with the longitudinal axis of the cradle 134. Cradle 134 is held in an elevated position by a column member 146, which comprises a lower vertical portion 148 and an upper angular portion 150. The upper angularly disposed portion 150 of the column 146 is sized so as to be contiguously located within the circular groove 144. The upper portion 150 of the column 146 is secured in the illustrated position to the cradle 134 by countersunk screws 152, which pass through apertures in the cradle 134 and are threadedly secured in threaded blind bores of the portion 150.

The lower end of the column portion 148 is secured to an oblong bearing plate 154 by a weldment 156. Accordingly, column 146 and bearing plate 154 are, in the illustrated embodiment, formed of aluminum, and alternatively of other rigid material including, for example, plastic or graphite compounds. Oblong bearing plate 154 is solid and generally of uniform thickness defining a top surface 158 and a bottom surface 160. Peripheral blunt edge 159 interconnects the top and bottom surfaces 158 and 160. Anti-displacement pedestals 21 are affixed to and fit in the recesses in the bottom surface 160 of the oblong bearing plate 154. FIG. 4 shows engagement of the top surface 24 of the base 22 with the anti-displacement pedestals 21, which occurs when the load of arm weight is imposed upon the cradle 134 at contoured concavity 136, to prevent movement of the bottom surface 160 relative to the top surface 24 of the base 22. This engagement allows the patient's arm to comfortably remain stationary while a patient is undergoing medical treatments. When no arm weight load is imposed upon the cradle 134 at the contoured concavity 136 there may be little or no engagement of the top surface 24 with the anti-displacement pedestals 21 to enable movement of the bottom surface 160 relative to the top surface 24 of the base 22. This permits facile adjustment of the cradle 134 to comfortably fit a variety of patients.

The otherwise smooth lower surface 160 of the oblong bearing plate 154 is interrupted by a boss 162, disposed below and in alignment with the lower portion 148 of the column 146. Boss 62 comprises an internal threaded blind bore 164. The carriage 30 further comprises a rotator/slider lower flange 166. See FIG. 4. Lower flange 166 is illustrated as generally having uniform thickness throughout comprising a top surface 170, a bottom surface 168, and a blunt edge 172 interconnecting surfaces 168 and 170.

The flange 166 comprises a centrally disposed upwardly directed boss 174, which has a central blind bore 176. The diameter of blind bore 176 is selected so as to snugly receive boss 162. At the base of blind bore 176 is disposed a countersunk bore 178 disposed in alignment with the threaded bore 164. A screw 180 is extended through counter-bore 178 so that the threaded shaft 182 thereof is snugly threaded received in bore 164. This is but one means of securing the oblong bearing plate 154 with the rotator/slider lower flange 166. Pins may be placed on the upward surface of the boss 174 and recesses may be created in the downward surface of the oblong bearing plate 154 to snugly receive the pins on the upward surface of the boss 174. As the flange 166 is translated, rotated, or both, so to are the remaining components of the carriage 130, including the cradle 134. Thus, the orientation of the carriage 130 may be manually set by the health care provider to suit the physical characteristics of the patient's upper arm to accommodate comfortable placement in the contoured concavity 136.

It should be kept in mind that flange 166 is disposed to translate, rotate, or both within the lower recess 74.

The boss 174 is surrounded by a detent collar 190, which merges with a stem 192, which has an internal bore 194, which is threaded and in which one or more biasing springs 196 are threadedly secured. The spring, directly adjacent the stem 192 holds and biases a spherical ball 198. Ball 198 seats in any one of a plurality of hemispherical recesses 200, providing for a releasible detent securing of the carriage 130 in any one of several available positions, i.e., the one most comfortable and most suited to the arm configuration of the patient. It is to be appreciated that collar 190 and stem 192 are slidably held in a groove in the base 22, disposed between the flange 166 and the oblong bearing plate 154. This allows the collar 190 and stem 192 to slide in the groove to allow a variety of positions.

Once either of the two carriages 130 has been suitably repositioned for a given patient, the health care provider can read the graduations 52, which may comprise two numerical measuring scales perpendicularly disposed to each other, and record the same on the patient's medical chart to provide precise identification as to the location and orientation of the bearing plate 154 for use in setting up the patient support 20 immediately prior to subsequent medical procedures involving the same patient.

Figure 3:
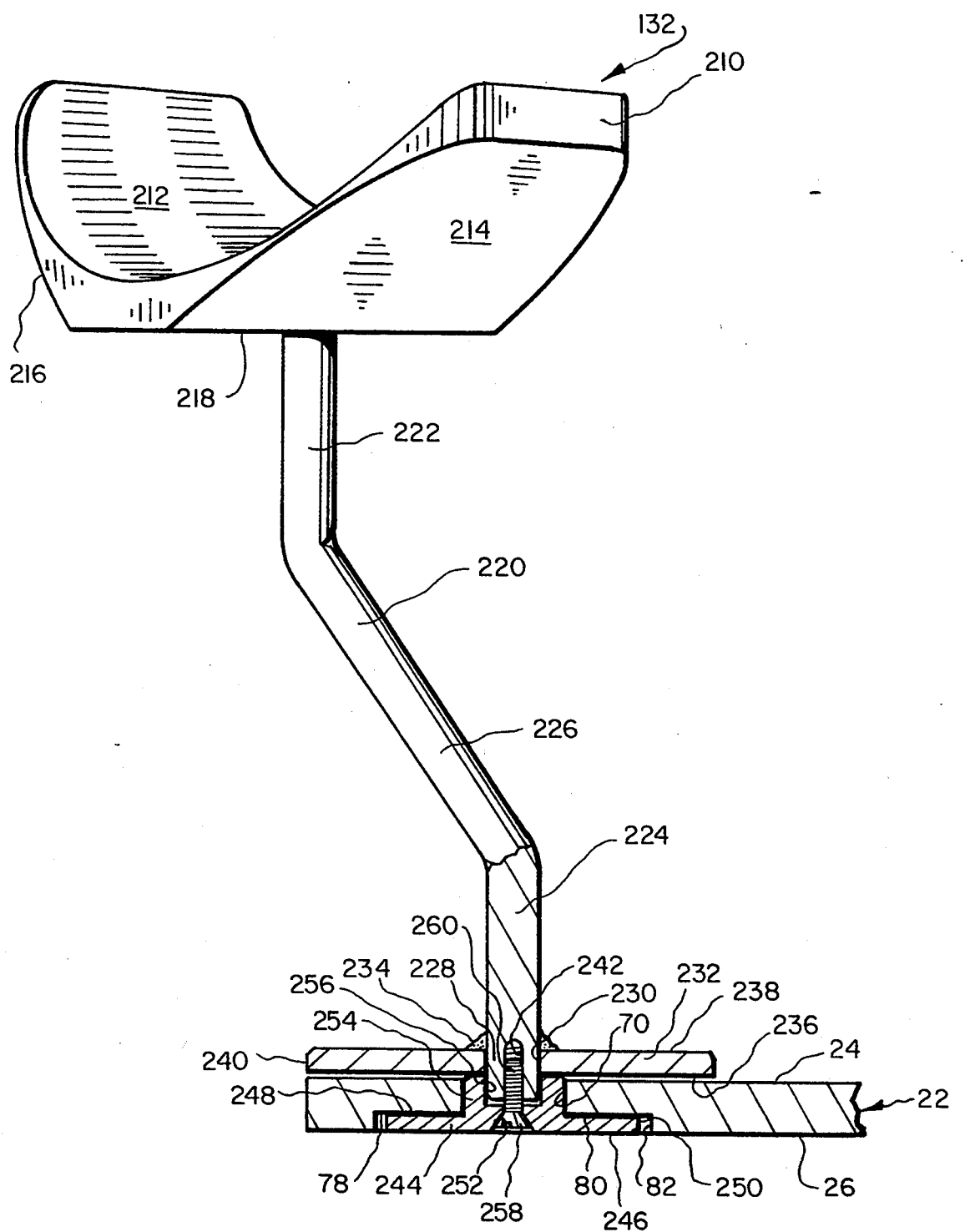
FIG. 3 is a cross-sectional view taken along lines 3—3 of FIG. 1.

Specific reference is now made to FIGS. 1 and 3 for the purpose of describing one of the two wrist support carriages 132. Each wrist support carriage 132 comprises a cradle 210. Cradle 210 comprises a contoured upwardly exposed concavity 212 sized and shaped to receive the wrist of a patient and oriented generally in a horizontal direction. Cradle 210 is preferably formed of plastic and comprises exterior converging side surfaces 214 and 216. The upper end of the column portion 222 comprises a threaded blind bore into which a countersunk screw 221 (FIG. 1) is threaded through an aperture in the cradle 210. Aluminum dog leg column 220, alternatively constructed with other durable and rigid material, including for example, plastic or graphite compounds, comprises a top and bottom, generally vertically directed, although offset segments 222 and 224, which are interconnected by a diagonal portion 226 which is disposed at an angle to both the horizontal and the vertical. The lower vertical section 224 comprises a lower end 228, which passes through a central aperture 230 in a disc-shaped aluminum bearing plate 232, alternatively constructed with other durable and rigid material, including for example, plastic or graphite compounds. The lower end 228 of the vertical portion 224 of the dog leg column 220 is secured to the bearing plate 232 by weldment 234, in the illustrated configuration. As can be seen from FIG. 3, the lower end 228 extends substantially below the bottom surface 236 of the bearing plate 232. Bearing plate 232 also comprises a top surface 238 which is illustrated as being horizontal and parallel to bottom surface 236. Bottom and top surfaces 236 and 238 are interconnected by a blunt peripheral edge 240.

The lower end 228 of the vertical column portion 224 comprises an upwardly directed blind bore 242.

The carriage 132 also comprises a slider/rotator flange 244, which is disposed, as illustrated in FIG. 3, in recess 78, described above. The thickness of the edges of the flange 244 are illustrated as being essentially the same as the depth of the recess 78. The flange 244 comprises a lower surface 246 and a top surface 248. Surfaces 246 and 244 are interconnected by a blunt flange 250.

The central portion of the flange 244 comprises a countersunk bore 252, which is in alignment with threaded bore 242. The flange 244 merges with an upwardly directed boss 254, which defines a central blind bore 256, the diameter of which accommodates snug reception of the exposed end 228. A countersunk screw 258 extends through the countersunk bore 252 and the threaded end 260 thereof is threadedly received in bore 242. When the screw 258 is firmly tightened, the flange 244 and the dog leg column 220 may be held firmly together, but allow the cradle 210 to freely move left or right or rotate to achieve a comfortable position for the patient. It is to be appreciated that when weight is placed upon the carriage 132, the lower surface 236 of the bearing plate 232 transfers the load to the base 22.

While no measuring or indexing graduations or scale is depicted in regard to either carriage 132, it is to be appreciated that having such indexing graduations or scale in conjunction with one or both of the carriages 132 falls well within the scope of the present invention.

The invention may be embodied in other specific forms without departing from the spirit or essential characteristics thereof. The present embodiments are, therefore, to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. A method of immobilizing the arms of a prone patient overhead during a medical procedure, comprising the steps of:
   providing a portable base adapted to be removably positioned on a patient support;
   placing the head of the patient above the base;
   relocating an adjustable head support with respect to the base to be disposed directly below the head of the patient;
   placing the head upon the relocated head support;
   placing the arms of the patient overhead and above the base;
   relocating adjustable arm supports with respect to the base to be disposed below the arms of the patient;
   placing the arms upon the relocated arm supports.

2. A method according to claim 1 further comprising the step of measuring the relocated head support position for later use in a further medical procedure with the patient.

3. A method according to claim 2 wherein the measuring step comprises reading a scale which depicts the relationship of the relocated head support and the base.

4. A method according to claim 1 wherein the first relocating step comprises rectilinearly translating the head support with respect to the base.

5. A method according to claim 1 further comprising the step of releasibly securing the head support in the relocated position.

6. A method according to claim 1 wherein the second placing step comprises contiguously supporting both the head and the neck of the patient.

7. A method according to claim 1 wherein the second relocating step comprises placing an arm support under each wrist and each upper arm of the patient.

8. A method according to claim 1 further comprising the step of movably associating each arm support with the base.

9. A method according to claim 1 wherein the second relocating step comprises translation at least in part and rotation at least in part.

10. A method according to claim 1 further comprising the step of measuring the relocated position of at least one arm support.

11. A method according to claim 10 wherein the measuring step comprises reading a scale showing the relocated relationship between the at least one arm support and the base.

12. A method according to claim 1 further comprising releasibly securing at least one arm support in the relocated position.

13. A method according to claim 1 further comprising stably positioning the base on the patient support.

14. A method according to claim 1 wherein the fourth placing step comprises cradling each arm at at least two spaced locations.

15. A patient support mechanism for use as an aid in performance of medical procedures comprising: a portable base adapted to be removably positioned on a patient support;
an adjustable head support carried by but movable with respect to the base to match the physical make-up of a patient;
a plurality of adjustable arm supports carried by but movable with respect to the base to match the location of the arms of the patient when the arms of the patient are positioned rearwardly of the patient's head and upwardly relative to the base.

16. A patient support mechanism according to claim 15 further comprising anti-displacement pedestals for underneath support of the base.

17. A patient support mechanism according to claim 15 wherein the base comprises a planar configuration.

18. A patient support mechanism according to claim 15 comprising slider structure by which the head support is linearly translated with respect to the base to accommodate selective positioning of the head support to be congruent with the disposition and characteristics of the head of the patient.

19. A patient support mechanism according to claim 18 comprising detent structure interposed between the slider structure and the base to releasibly restrain the head support in a desired position to suit the patient.

20. A patient support mechanism according to claim 15 comprising measuring structure by which a selected head support position can be measured for later use with the same patient.

21. A patient support mechanism according to claim 20 wherein the measuring structure comprises an exposed graduated scale.

22. A patient support mechanism according to claim 15 comprising structure accommodating selective linear translation and rotation of at least one of the arm supports with respect to the base.

23. A patient support mechanism according to claim 22 comprising detent structure interposed between the structure accommodating linear translation and rotation and the base to releasibly restrain the at least one arm support in a desired position congruent with the arm position of the patient.

24. A patient support mechanism according to claim 20 further comprising measuring structure by which a selected position of the at least one arm support can be measured for subsequent use.

25. A patient support mechanism according to claim 15 wherein at least one arm support comprises an elevated cradle comprising a concavity sized and shaped to match a portion of an arm of the patient.

26. A patient support mechanism according to claim 25 wherein the cradle is supported in an elevated position by column a structure.

27. A patient support mechanism according to claim 25 wherein the arm supports comprise two sets of two opposed arm supports, one of each set comprising a movable wrist support and the other a movable upper arm support.

* * * * *